US008057477B2

(12) United States Patent
Desarzens et al.

(10) Patent No.: US 8,057,477 B2
(45) Date of Patent: *Nov. 15, 2011

(54) GUIDED REAMER SYSTEM FOR RESHAPING BONE (75) Inventors: Yves Desarzens, Corgémont (CH); André Lechot, Orvin (CH)

(73) Assignee: Greatbatch Medical S.A., Orvin (CH)

( * ) Notice: Subject to any disclaimer, the term of this patent is extended or adjusted under 35 U.S.C. 154(b) by 411 days.

This patent is subject to a terminal disclaimer.

(21) Appl. No.: 11/117,740

(22) Filed: Apr. 29, 2005

(65) Prior Publication Data

US 2005/0251145 A1  Nov. 10, 2005

Related U.S. Application Data (63) Continuation-in-part of application No. 10/441,148, filed on May 19, 2003, now Pat. No. 7,115,119, which is a continuation-in-part of application No. 10/391,464, filed on Mar. 18, 2003, now Pat. No. 7,056,317, which is a continuation of application No. 09/902,369, filed on Jul. 9, 2001, now Pat. No. 6,540,739, which is a continuation of application No. 09/602,341, filed on Jun. 24, 2000, now Pat. No. 6,264,647.

(51) Int. Cl.
  *A61B 17/00* (2006.01)
(52) U.S. Cl. ........................................ 606/80

(58) Field of Classification Search .......... 606/1, 79–81; 623/16.11–23.63
  See application file for complete search history.

(56) References Cited

U.S. PATENT DOCUMENTS

| 4,023,572 | A  | * | 5/1977  | Weigand et al. | 606/81  |
| 5,180,384 | A  | * | 1/1993  | Mikhail        | 606/80  |
| 5,514,141 | A  | * | 5/1996  | Prizzi, Jr.    | 606/80  |
| 5,658,290 | A  | * | 8/1997  | Lechot         | 606/80  |
| 5,976,143 | A  | * | 11/1999 | McCue          | 606/80  |
| 6,106,536 | A  | * | 8/2000  | Lechot         | 606/180 |
| 6,475,221 | B1 | * | 11/2002 | White et al.   | 606/80  |
| 6,854,742 | B2 | * | 2/2005  | Salyer et al.  | 279/93  |
| 7,918,856 | B2 | * | 4/2011  | Guelat et al.  | 606/80  |
| 2004/0193168 | A1 | * | 9/2004 | Long et al.    | 606/80  |

FOREIGN PATENT DOCUMENTS

| EP | 0 782 840 A1 | 7/1997 |
| WO | WO 2004/032767 | 4/2004 |

* cited by examiner

*Primary Examiner* — Thomas C. Barrett
*Assistant Examiner* — Michael Araj
(74) *Attorney, Agent, or Firm* — Michael F. Scalise (57) ABSTRACT A reamer system is provided which includes a cannulated reamer holder, and a corresponding cannulated reamer, which, when assembled and operated over a drill pin secured in a manner axially aligned with the stem of the femoral joint, enables the accurate and controlled reshaping of the femoral joint. The reamer is made up of a cutting form and a central guide, in which the guide is supported at the center of the cutting form by a bar structure. The bar structure includes portions which connect to and extend radially between the central guide and a peripheral edge of the cutting form.

18 Claims, 7 Drawing Sheets

GUIDED REAMER SYSTEM FOR RESHAPING BONE

CROSS REFERENCE TO RELATED APPLICATIONS

This application is a continuation-in-part of U.S. patent application Ser. No. 10/441,148 filed May 19, 2003, now U.S. Pat. No. 7,115,119 entitled Dual Reamer Holder for Surgical Use which is a continuation-in-part of U.S. patent application Ser. No. 10/391,464, entitled Instrument Holder for a Surgical Instrument, filed on Mar. 18, 2003, now U.S. Pat. No. 7,056,317, which is in turn continuation of Ser. No. 09/902,369 filed on Jul. 9, 2001, now U.S. Pat. No. 6,540,739, which in turn is a continuation of Ser. No. 09/602,341 filed Jun. 24, 2000 and now U.S. Pat. No. 6,264,647 issued Jul. 24, 2001, the contents of all of the above applications and patents being incorporated herein by reference thereto.

BACKGROUND OF THE INVENTION

The invention relates to a bone shaping system made up of an instrument holder and a surgical instrument for attachment to the holder. The holder includes a shank equipped with a head designed to receive an instrument, and an annular locking component mounted so as to slide about the shank, under the head, equipped with locking means which cooperate with the head so as to lock the instrument on the head, and pushed against the head by a helical spring.

One such system is described in European Patent 0782840, the content of which is incorporated herein by reference thereto, and includes a shaft (10), equipped at one end with a cutting head holder (12) which has a bayonet joint and lock. A hemispherical or conical rotary cutting head (1) has inner radial rods (4) to engage with the bayonet joint. The cutting head contains an axial guide tube (5) between the inner ends of the radial rods and a central aperture (3) to receive a twist drill (9) which makes a hole in the middle of the recess formed by the cutting head. The lower end of the guide tube has one or more notches to receive corresponding studs on the twist drill so they rotate together. The holder (12) has a projection to block the drill in the guide tube. Additionally, the end of the guide tube, which adjoins the centre of the cutting head, has at least two projecting cutting teeth. Where a central hole in the recess is not required, a shorter twist drill is employed. However, while useful for controlling the cutting of the acetabulum, this system does not foresee a sliding fit between the reamer and the twist drill but rather one in which the two rotate together as a unit. Further, it is not contemplated that the drill be affixed to the bone and subsequently be used for guidance.

Other systems provide for reshaping of the bone, but the tool itself generally obstructs the view of the femoral lobe during cutting.

Therefore, there is a needed for cutters capable of cutting and shaping the femoral joint in preparation for the reception of a prosthetic cap. Such an application presents other challenges in guidance and control, particularly that of ensuring that the stem of the femoral joint is not damaged in the process.

What is needed therefore is a system which enables controlled cutting and reshaping of the femoral joint in preparation for the reception of a femoral cap prosthesis. What is needed is a system which does not completely obstruct the view of the femoral lobe when the reamer is placed over the lobe, ready for cutting or process thereof. Further, what is needed is a system that controls heat by moving any points of heat generation from the reamer to the holder, and thus away from the operative site.

SUMMARY OF THE INVENTION

A reamer system is provided which includes a cannulated reamer holder, and a corresponding cannulated reamer, which, when assembled and operated over a drill pin secured in a manner axially aligned with the stem of the femoral joint, enables the accurate and controlled reshaping of the femoral joint. The reamer is made up of a cutting form and a central guide, in which the guide is supported at the center of the cutting form by a bar structure. The bar structure includes portions which connect to and extend radially between the central guide and a peripheral edge of the cutting form. Optionally, the central guide includes a surface offset from a plane of the bar structure to a degree which enables that surface to contact an associated surface referenced to the bone, in order to prevent the cutting form from plunging so far over the bone as to potentially damage the femoral stem. This offset surface is preferably polished to reduce friction during relative rotational movement between this surface and the surface referenced to the bone. The offset surface is an axially perpendicular surface of a boss through which the drill pin is guided.

In a feature, the system provides a guidance surface in the holder and not primarily in the reamer, thus enabling moving a region of heat generation away from the cutting site, into the holder.

DETAILED DESCRIPTION OF THE PREFERRED EMBODIMENT(S)

Figures 1, 2A:
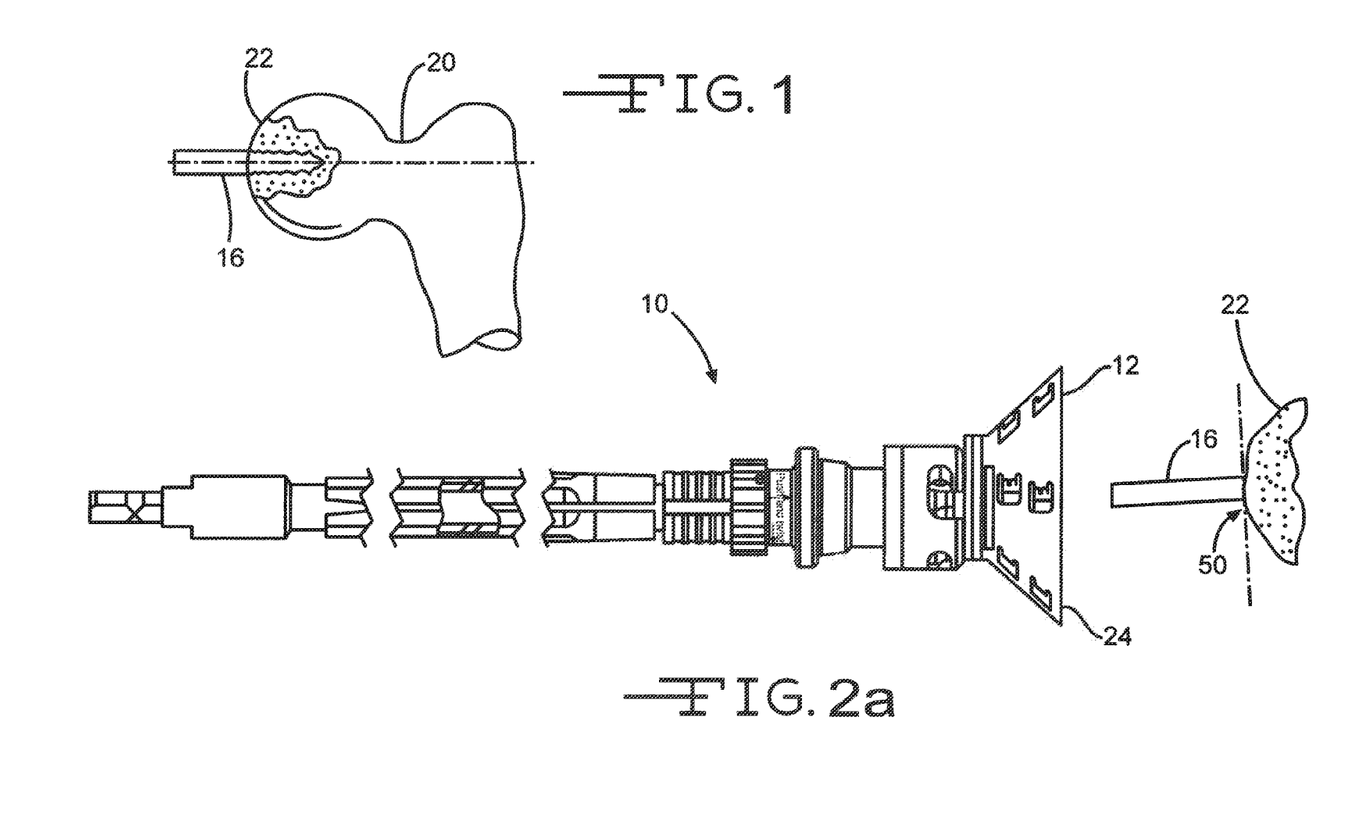
FIG. 1 is a schematic view of a femoral joint into which a bone pin is inserted.
FIG. 2*a* is a side view of the system of the invention ready to be received at the operative site.

Referring now to FIG. 1, instead of a total hip replacement, which removes the organic stem 20 of a femoral joint 22 replacing it with an artificial one, processes exist that attempt to preserve the natural joint. One such procedure places a hard, external cap (not shown, but having an eternal spherical form which mates with a socket on its external side and over a resurfaced femoral joint via its internal surfaces). The cap is often made of metal and has precise interface dimensions which must be created on the bone in order for the cap to properly fit over the joint and to properly function in its corresponding prosthetic socket. A drill pin 16 is affixed to the joint 22, axially to the stem 20, in order to prevent damage to the stem, and to guide the cutting tool to precisely shape the joint.

Referring now to FIGS. 2a-2c and 3a-3c, the system 10 of the invention includes a cannulated reamer 12 and a cannulated reamer holder 34. The cannulated reamer 12 has a central cannulation 14 which is a recess adapted to receive a drill pin 16 secured in a manner axially aligned with the stem 20 of the femoral joint 22. The reamer 12, has a profile cutting form 24 and a central axial guide 26. The guide 26 is supported at a center of the cutting form 24 by a bar structure 30. The bar structure 30 has portions or bars 32 which connect to and extend radially from the central guide 26 and which non-rotatably connect to the cutting form 24.

Figure 2B:
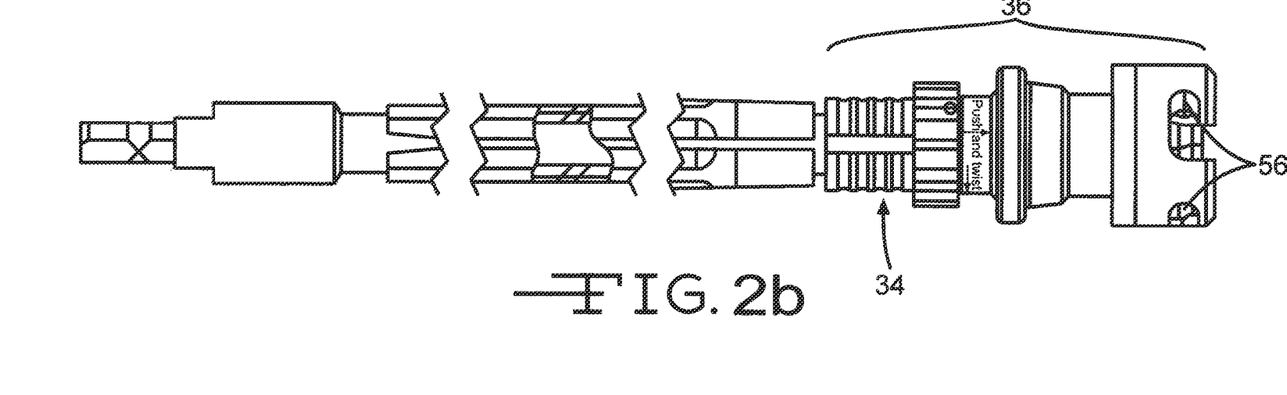
FIG. 2*b* is a side view of the reamer holder of the system of the invention.
Figure 2C:
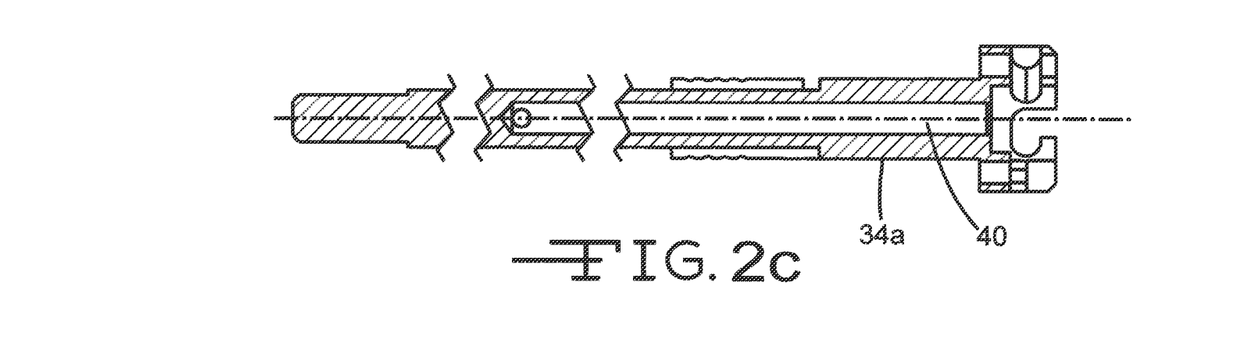
FIG. 2*c* is a side view of the shaft 34*a* of the holder of the system of the invention.

The cannulated reamer holder 34 has a bayonet locking device 36 capable of locking the holder 34 to the cannulated reamer 12 and a corresponding central cannulation 40, permitting the drill pin 16 to pass therethrough. The bayonet locking mechanism 36 includes recesses 56 which catch portions of the bar structure 30.

Figure 3A:
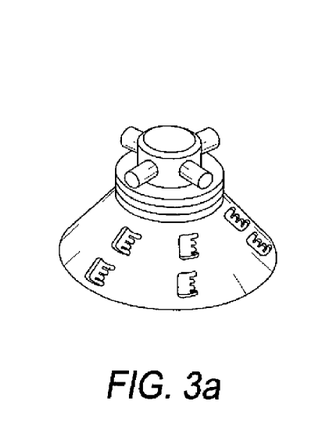
FIG. 3*a* is a perspective view of a reamer of the system of the invention.
Figure 3B:
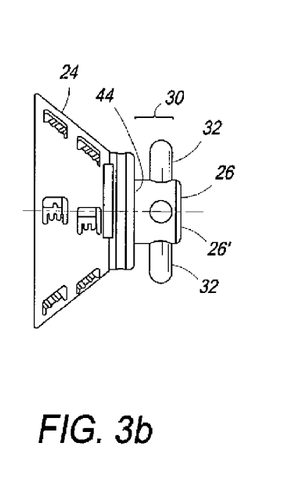
FIG. 3*b* is a side view of a reamer of the system of the invention.
Figure 3C:
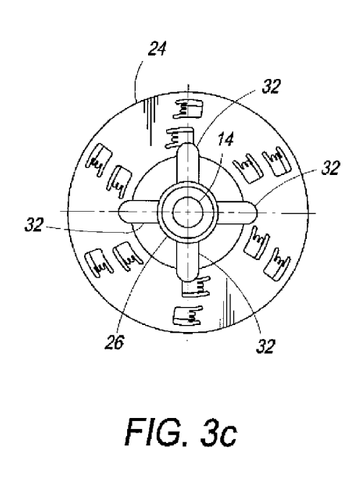
FIG. 3*c* is a top view of a reamer of the system of the invention.
Figure 4A:
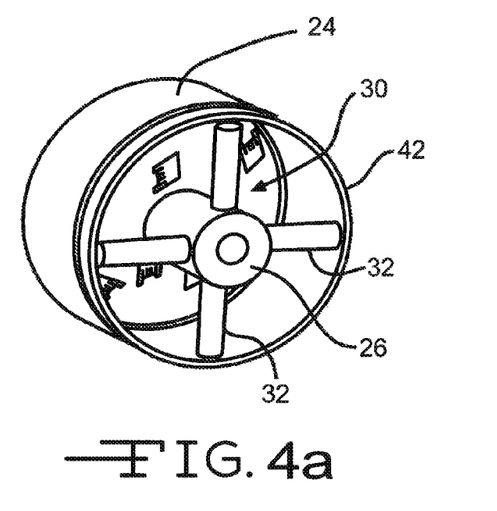
FIG. 4*a* is a perspective view of an alternate reamer of the system of the invention.
Figure 4B:
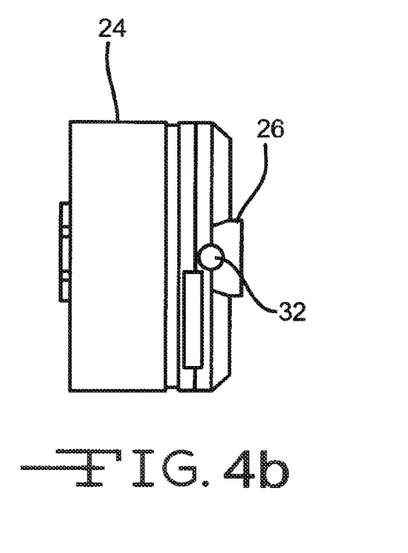
FIG. 4*b* is a side view of the alternate reamer of the system of the invention.
Figure 4C:
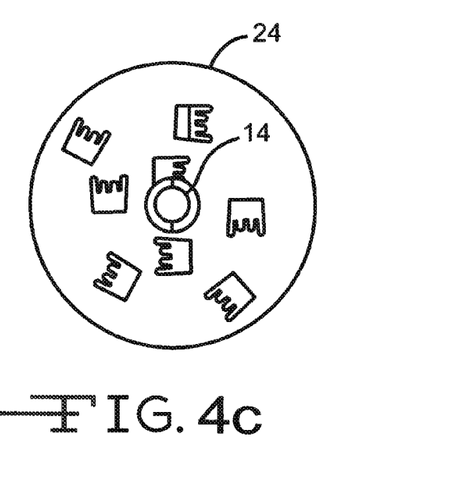
FIG. 4*c* is a top view of the alternate reamer of the system of the invention.

The bar structure 30 is made up of a hollow post 26' attached to an apex 44 of the cutting form 24. The post has bars 32 attached thereto which are axially spaced apart and extend radially out from the post.

Referring in particular to the embodiments shown in FIGS. 4a-9, some of the bars 32 of the bar structure 30 extend and connect between the central guide 26 and a peripheral edge 42 of the cutting form 24.

Figure 5A:
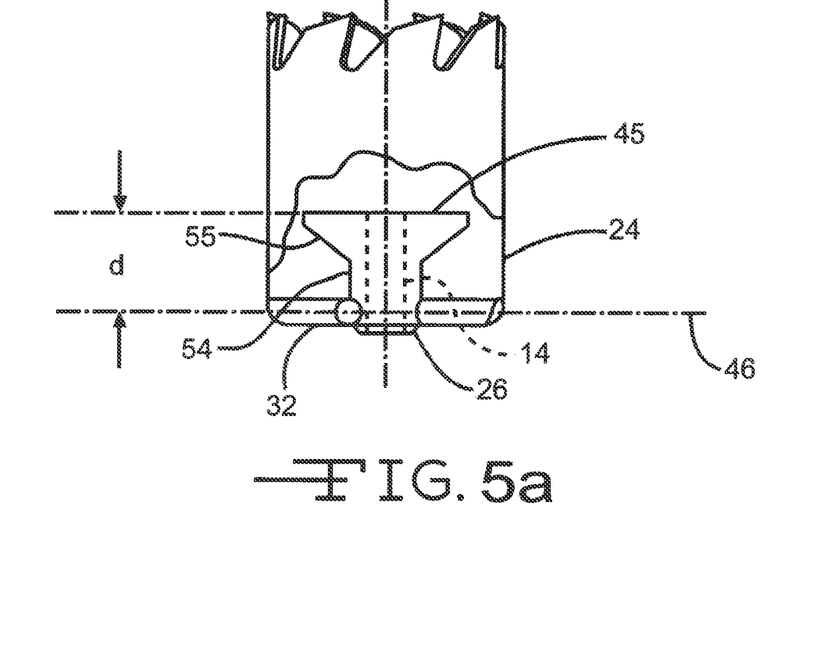
FIG. 5*a* is a partial cutaway, side view of a second alternate reamer of the system of the invention.
Figure 5B:
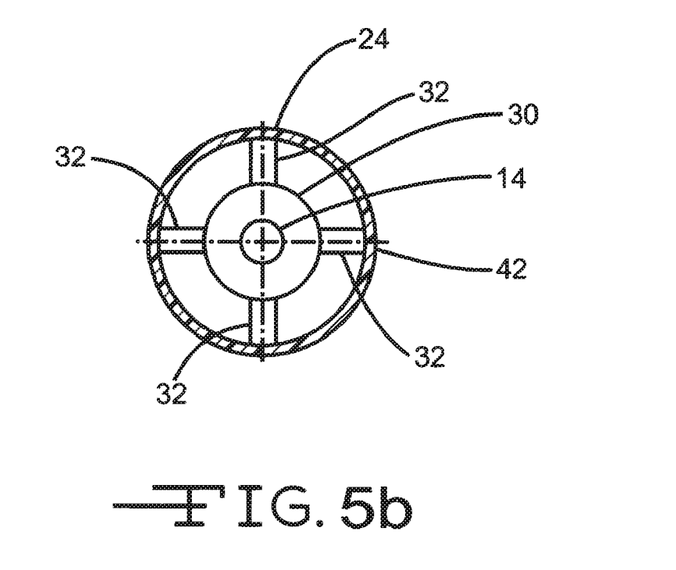
FIG. 5*b* is a top view of the second alternate reamer of the system of the invention.

Referring now to FIG. 5a, the central guide 26 includes a surface 44 offset from a plane 46 of the bar structure 30 at a distance d which enables that surface 44 to contact an associated surface 50 referenced to the bone 22, in order to prevent the cutting form 24 from plunging so far over the bone as to potentially damage the femoral stem 20. The offset surface 44 is preferably polished to reduce friction during relative rotational movement between this surface 44 and the surface 50 referenced to the bone 22. The offset surface 44 is an axially perpendicular surface of a boss 52 optionally possessing a flange 54 through which the drill pin 16 is guided via the central cannulation 14 therethrough.

In a preferred embodiment, the reamer handle 34 has the central cannulation 14 being polished or otherwise made to closely fit over the drill pin 16, so as to provide substantially all the guidance thereof. Thus, heat which is generated is generated in the holder away from the operative site and thus less likely to cause damage to tissue or bone.

Figure 6:
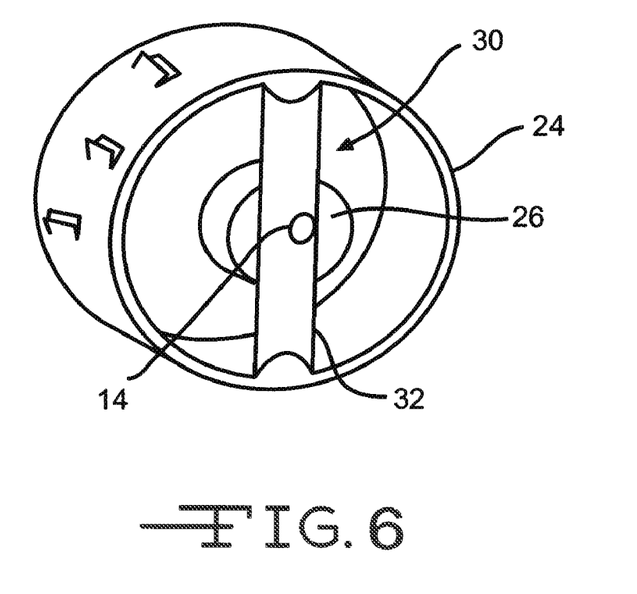
FIG. 6 is a perspective view of a third alternate reamer of the system of the invention.

Referring now to FIG. 6, the bar structure 30 is made up of a single bar 32, traversing a center of the cutting form 24. The central axial guide 26 includes a central cannulation 14 in the bar 32.

Figure 7:
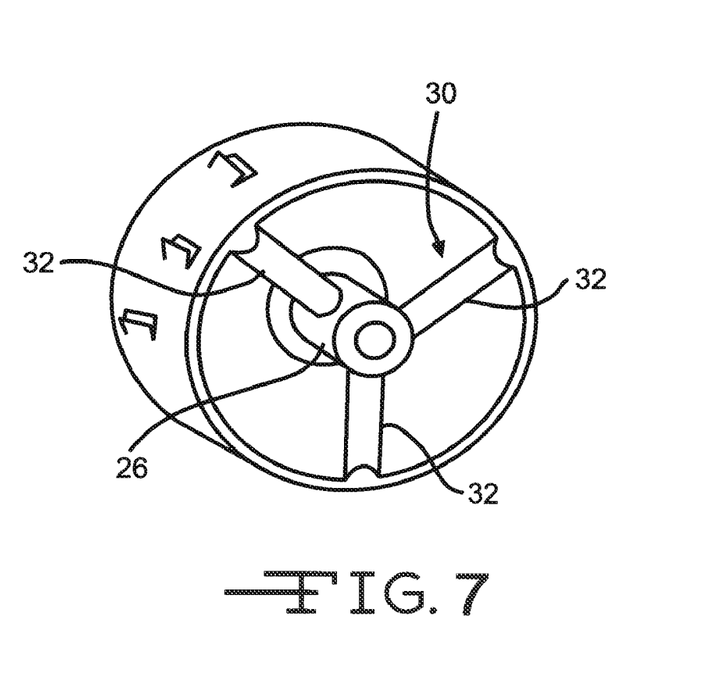
FIG. 7 is a perspective view of a fourth alternate reamer of the system of the invention.

Referring now to FIG. 7, the bar structure 30 is made up of three bars 32 connected to the central axial guide 26.

Figure 8:
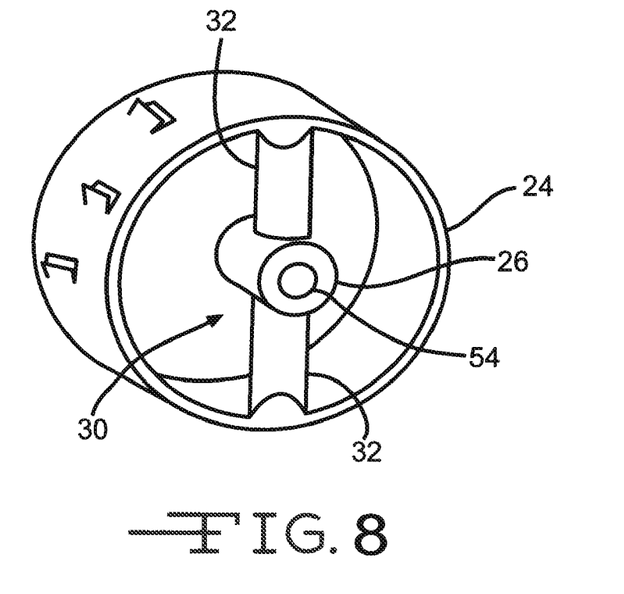
FIG. 8 is a perspective view of a fifth alternate reamer of the system of the invention.

Referring now to FIG. 8, the bar structure 30 is made up of at least two bars 32 traversing a center of the cutting form 24 and connected to the central axial guide 26 which has a central cannulation 14 for receiving a drill pin 16.

Referring now to FIGS. 4a-4c, and 5a and 5b, the bar structure 30 is made up of four bars 32 connected to the central axial guide 26.

Figure 9:
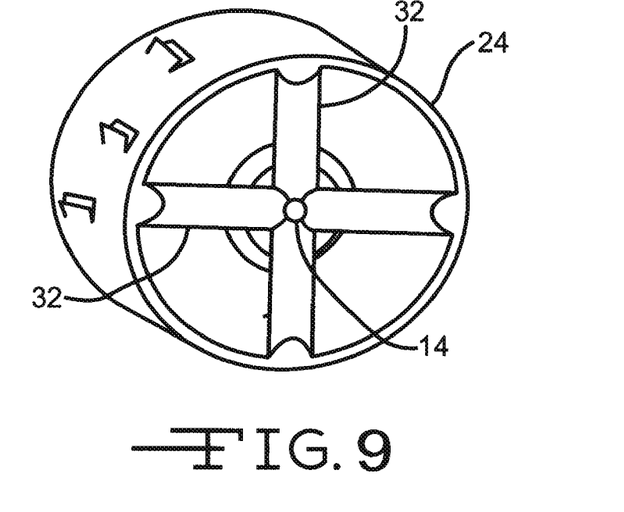
FIG. 9 is a perspective view of a sixth alternate reamer of the system of the invention.

Referring now to FIG. 9, the bar structure 30 is made up of two cross bars 32 which intersect at a center of the cutting form 24. The guide 26 includes a central cannulation 14 at the intersection of the bars 32.

Optionally, the cannulation 40 in the holder 34 is sized and surface treated to be a precise, sliding fit with the drill pin 16, in order to provide substantially all axial guidance to the reamer 12 when cutting bone such as the femoral joint 22.

In another variation, the cannulation 14 in the reamer 12 is a clearance hole.

Alternatively, the cannulation 14 in the reamer 12 is sized and surface treated to be a precise, sliding fit with the drill pin 16, in order to provide substantially all the axial guidance to the reamer when cutting bone.

Unlike a traditional reamer. (not shown) which cuts a concave form in a bone socket using a convex reamer, a profile cutting form 24 cuts a convex form on the external surfaces of bone using a concave reamer. In other words, the profile cutting reamer cuts a surface which is cylindrical or convex, characterized by having a second derivative which is a positive number, as opposed to a traditional acetabular reamer which cuts a concave form, characterized as having a negative second derivative. Consequently, as mentioned above, the system, designed to cut concave surfaces, is quite different from prior art systems which cut convex surfaces.

In an advantage, the system 10 enables controlled cutting of the femoral joint, while avoiding damage to the femoral stem.

In another advantage, the holder 34 of the invention is easily disassembled for cleaning and sterilization.

In another advantage, polished surfaces, particularly in the reamer holder, move heat buildup from the reamer to the holder itself, helping prevent damage to tissue and bone at the operative site.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A reamer, which comprises:
    a) a cutting form extending distally and outwardly from a proximal cutting form portion having a first diameter to a distal edge having a second, greater diameter;
    b) an axial guide having a guide length extending from a proximal guide end to a distal guide end, wherein the proximal cutting form portion is connected to the distal guide end; and
    c) at least two radial bars, each having a proximal radial bar end attached to the axial guide and a distal radial bar end that is not connected to either the axial guide or the cutting form.

2. The reamer of claim 1 wherein the axial guide is comprised of a hollow post attached to the proximal cutting form portion at the first diameter, the hollow post having the radial bars attached thereto which are axially spaced apart and extend radially out from the post.

3. The reamer of claim 1 wherein the central cannulation in the reamer is a clearance hole.

4. The reamer of claim 1 wherein the central cannulation in the reamer is sized and surface treated to be in a precise, sliding fit with a drill pin.

5. The reamer of claim 1 wherein there are four radial bars extending outwardly from the axial guide.

6. The reamer of claim 5 wherein the four radial bars are disposed at 90° with respect to each other.

7. The reamer of claim 1 wherein the at least two radial bars extend in a plane at an intermediate location between the proximal guide end and the distal guide end.

8. The reamer of claim 1 wherein the cutting form includes a plurality of cutting teeth.

9. The reamer of claim 1 wherein the axial guide comprises a central cannulation that passes from the proximal guide end to and through the distal guide end connected to the proximal cutting form portion.

10. A reamer, which comprises:
   a) a cutting form extending distally and outwardly from a proximal cutting form portion having a first diameter to a distal edge having a second, greater diameter;
   b) an axial guide having a guide length extending from a proximal guide end to a distal guide end, wherein the proximal cutting form portion is connected to the distal guide end;
   c) four radial bars, each having a proximal radial bar end attached to the axial guide and a distal radial bar end that is not connected to either the axial guide or the cutting form; and
   d) a central cannulation that passes from the proximal guide end to and through the distal guide end connected to the proximal cutting form portion.

11. The reamer of claim 10 wherein the radial bars are disposed at 90° with respect to each other extending outwardly from the axial guide.

12. The reamer of claim 10 wherein the radial bars extend in a plane at an intermediate location between the proximal guide end and the distal guide end.

13. The reamer of claim 10 wherein the cutting form includes a plurality of cutting teeth.

14. A reamer system, which comprises:
   a) a reamer, comprising
      i) a cutting form extending distally and outwardly from a proximal cutting form portion having a first diameter to a distal edge having a second, greater diameter;
      ii) an axial guide having a guide length extending from a proximal guide end to a distal guide end, wherein the proximal cutting form portion is connected to the distal guide end;
      iii) at least two radial bars extending radially outwardly from the axial guide, intermediate the proximal guide end and the distal guide end, wherein each radial bar has a proximal bar end attached to the axial guide and a distal bar end that is not connected to either the axial guide or the cutting form; and
      iv) a central cannulation that passes from the proximal guide end to and through the distal guide end connected to the proximal cutting form portion; and
   b) a reamer holder having a bayonet locking mechanism capable of locking the holder to the reamer at the radial bars.

15. The reamer system of claim 14 wherein the reamer holder has a central cannulation permitting a drill pin to pass therethrough.

16. The reamer system of claim 15 wherein the cannulation in the holder is sized and surface treated to be in a precise, sliding fit with a drill pin.

17. The reamer system of claim 14 wherein the cutting form of the reamer includes a plurality of cutting teeth.

18. The reamer of claim 14 wherein the bayonet locking mechanism includes recesses which catch portions of the bars.

* * * * *